US010265088B2

(12) United States Patent
Ciulla et al.

(10) Patent No.: US 10,265,088 B2
(45) Date of Patent: Apr. 23, 2019

(54) MEDICAL RETRIEVAL SYSTEMS AND RELATED METHODS

(71) Applicant: Boston Scientific Scimed, Inc., Maple Grove, MN (US)

(72) Inventors: Ronald Ciulla, Westford, MA (US); Timothy James McCaslin, Dedham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 264 days.

(21) Appl. No.: 14/975,005

(22) Filed: Dec. 18, 2015

(65) Prior Publication Data

US 2016/0174956 A1 Jun. 23, 2016

Related U.S. Application Data

(60) Provisional application No. 62/094,696, filed on Dec. 19, 2014.

(51) Int. Cl.
| | | |
|---|---|---|
| A61B 17/00 | (2006.01) | |
| A61B 18/24 | (2006.01) | |
| A61B 17/221 | (2006.01) | |
| A61B 17/50 | (2006.01) | |
| A61B 1/00 | (2006.01) | |
| A61B 1/005 | (2006.01) | |

(52) U.S. Cl.
CPC .......... *A61B 17/221* (2013.01); *A61B 1/0052* (2013.01); *A61B 1/00135* (2013.01); *A61B 17/50* (2013.01); *A61B 1/0055* (2013.01); *A61B 18/24* (2013.01); *A61B 2017/003* (2013.01); *A61B 2017/0046* (2013.01); *A61B 2017/00424* (2013.01); *A61B 2017/2212* (2013.01)

(58) Field of Classification Search
CPC .................................................. A61B 1/0052
See application file for complete search history.

(56) References Cited

U.S. PATENT DOCUMENTS

| | | | |
|---|---|---|---|
| 7,094,202 B2 | 8/2006 | Nobis et al. | |
| 8,512,350 B2 | 8/2013 | Ward | |
| 2002/0183593 A1* | 12/2002 | Chin | A61B 1/00071 600/145 |
| 2013/0046297 A1 | 2/2013 | Lingeman et al. | |
| 2013/0184691 A1* | 7/2013 | Oskin | A61B 17/00234 606/1 |
| 2014/0114126 A1 | 4/2014 | Dresher | |
| 2014/0171735 A1 | 6/2014 | Galperin et al. | |

\* cited by examiner

*Primary Examiner* — Scott T Luan
(74) *Attorney, Agent, or Firm* — Bookoff McAndrews, PLLC

(57) ABSTRACT

An apparatus may include a handle having a first portion and a second portion. The second portion may extend at an angle from the first portion. The handle may also include a passage configured to receive a medical device therethrough and defined by the first portion. Further, the handle may include an actuator operably coupled to the first portion. The apparatus may also include an endoscopic insertion device coupled to and extending distally of the first portion of the handle. Further, manipulation of the actuator may be configured to deflect a distal portion of the insertion device.

20 Claims, 6 Drawing Sheets

MEDICAL RETRIEVAL SYSTEMS AND RELATED METHODS

CROSS-REFERENCE TO RELATED APPLICATIONS

The application claims the benefits of priority from U.S. Provisional Application No. 62/094,696, filed on Dec. 19, 2014, the entirety of which is incorporated herein by reference.

TECHNICAL FIELD

Various aspects of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Retrieval devices are also used in lithotripsy and ureteroscopy procedures to treat urinary calculi (e.g., kidney stones) in the ureter of a patient.

Ureteroscopy, for example, may be performed to diagnose and treat urinary tract diseases and ureteral strictures. A ureteroscope may be inserted retrograde through the urinary tract such that diagnosis and treatment of urinary tract abnormalities may be performed. Current flexible ureteroscopes require two hands to control the ureteroscope. Usually, the dominant hand will hold the handle of the ureteroscope while the non-dominant hand holds the distal portion of the ureteroscope as it enters the urethral meatus. If the medical professional determines there is a need to insert a tool such as a basket, grasper, or forceps through the working channel of the scope, he or she is left to either remove the non-dominant hand from the urinary meatus or instruct an assistant to hold the tool handle.

Removing their hand from the urinary meatus, however, removes the medical professional's ability to control the depth of the scope's insertion into the urinary meatus. On the other hand, if the medical professional opts to instruct an assistant to control the medical tool, for example, a basket, communication between the medical professional and assistant must be exact and clear, otherwise, the assistant may be required to perform multiple attempts at grasping a stone or other material before successfully capturing the stone or other material within the basket. Multiple attempts frequently result in damaged baskets, increased risk of damage to the patient's surrounding tissue, and increased time of procedure, among others.

In addition, conventional ureteroscopes are designed to be held in the vertical or upright position which necessitates that the medical professional tightly flex his or her arm at the elbow to bring their forearm parallel to their body and bend their wrist outward to grasp the ureteroscope. Distal tip scope deflection may be achieved via an actuator on the proximal end of the scope by the medical professional's index finger or thumb. As the medical professional rotates the ureteroscope, he or she may experience wrist angulation resulting in painful symptoms similar to those of carpal tunnel. Holding the ureteroscope in such an upright position may also interfere with the medical professional's intuitive connection between the motion of their hand, and the resultant motion of a distal tip of the ureteroscope. It also precludes them from controlling the depth and rotation of any instrument inserted into the ureteroscope and the depth of the scope at the same time. End deflection and scope rotation is controlled by the dominant hand. The assistant manages the mechanical actuation of the instrument (opening and closing of graspers, baskets, scissors, loops, etc.).

The systems and methods of the current disclosure may rectify some of the deficiencies described above.

SUMMARY

Examples of the present disclosure relate to, among other things, medical retrieval systems and related methods of use. Each of the examples disclosed herein may include one or more of the features described in connection with any of the other disclosed examples.

In one example, an endoscopic apparatus may include a handle having a first portion and a second portion. The second portion may extend at an angle from the first portion. The handle may also include a passage configured to receive a medical device therethrough and defined by the first portion. Further, the handle may include an actuator operably coupled to the first portion. The apparatus may also include an insertion device coupled to and extending distally of the first portion of the handle. Further, manipulation of the actuator may be configured to deflect a distal portion of the insertion device.

Examples of the endoscopic apparatus may additionally or alternatively include one or more of the following features: the angle (between the first and second portions) may be between about 35° and about 55°; the passage may be defined along an outer surface of the first portion; the passage may be configured to receive the medical device therein along an angle relative to a longitudinal axis of the insertion device; the angle relative to the longitudinal axis of the insertion device is between about 0° and about 45°; the passage may be configured to rotatably receive the medical device therein; the actuator may comprise at least one of trigger, ring, rocker, and joystick; the actuator may be configured for at least two-way deflection of the distal portion of the insertion device; the passage may be configured to receive the medical device therein via a snap-fit connection; the passage may extend through an inner central portion of the first portion of the handle; an opening may extend through the first portion of the handle, the opening may be in communication with the channel; a slot may extend proximally from a proximal end of the opening and configured to receive an actuation mechanism of the medical device therein; the actuator may be operably coupled to a proximal end of first portion of the handle; the medical device may comprise a retrieval basket and/or a laser fiber; and the handle may comprise a clam-shell construction.

In another example, an endoscopic apparatus may comprise a handle comprising a handle housing. The handle housing may define a central base portion, a first extension, and a second extension. The first extension and the second extension may extend from opposite sides of the base portion and may be configured to be grasped by opposite hands of a user. The handle may include a passage configured to receive a medical device therethrough. The passage may be positioned adjacent to one or the other of the first extension and the second extension. The handle may also include an actuator. The actuator may be positioned adjacent to other of the first extension and the second extension. The apparatus may also include an insertion device coupled to and extending distally of the first portion of the handle. Manipulation of the actuator may be configured to deflect a distal portion of the insertion device.

Examples of the endoscopic apparatus may additionally or alternatively include one or more of the following features: the passage may be configured to rotatably receive the medical device therein; the actuator may be configured for at least two-way deflection of the distal portion of the insertion device; the passage may be configured to receive the medical device therein via a snap-fit connection; the handle may include a clam-shell construction; and the medical device may include a retrieval basket and/or a laser fiber.

In a further example, a method may include delivering an endoscopic insertion device into an anatomical opening. The insertion device may have a deflectable distal portion and a proximal handle. The proximal handle may include a first portion and a second portion. The second portion may extend at an angle from the first portion. Additionally, the handle may include a passage configured to receive a medical device therethrough and may be defined by the first portion. Further, the handle may include an actuator operably coupled to the first portion. The method may also include manipulating the deflectable distal portion via the actuator and transitioning the medical device between a retracted state and an extended state distally of the distal portion of insertion device.

Examples of the system may additionally or alternatively include one or more of the following features: the medical device may comprise a basket, and the method may further include capturing an object within the basket; and the passage may be configured to rotatably receive the medical device therein.

It may be understood that both the foregoing general description and the following detailed description are exemplary and explanatory only and are not restrictive of the claimed features.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Overview

Examples of the present disclosure relate to a medical system for diagnosing and/or treating internal areas of a subject's body. The medical system may include a medical device and an insertion device for facilitating ergonomic manipulation and intuitive control by a medical professional during a procedure.

Detailed Examples

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

Figure 1:
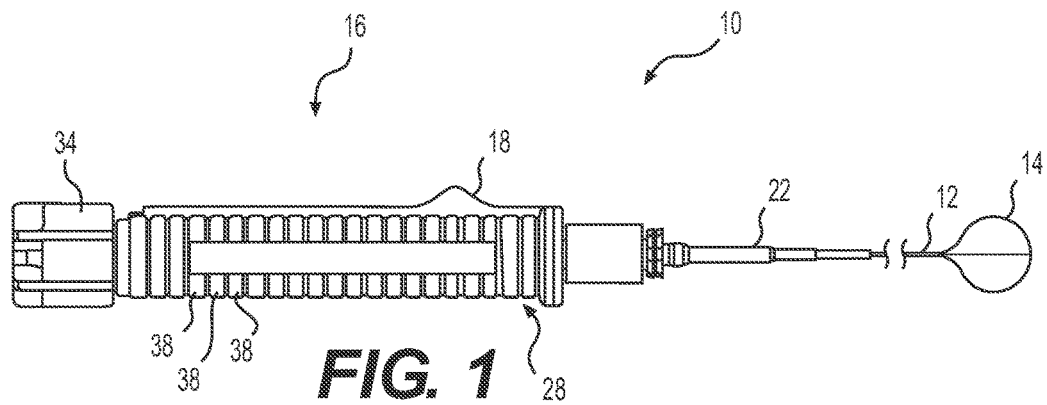
FIG. 1 illustrates an exemplary medical device.
Figure 2:
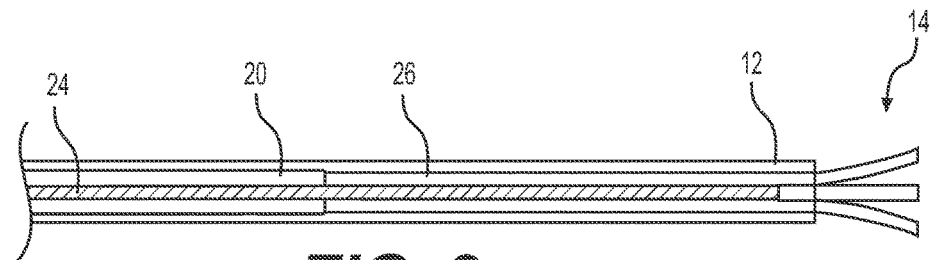
FIG. 2 illustrates a cross-sectional view of a portion of the exemplary medical device of FIG. 1.
Figure 3:
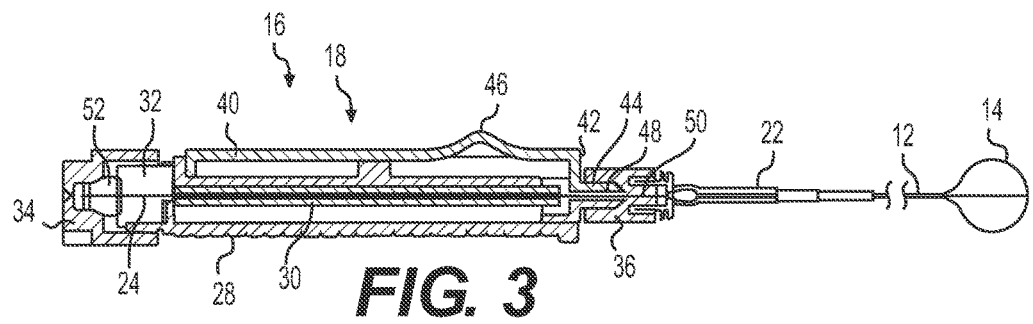
FIG. 3 illustrates a cross-sectional view of another portion of the exemplary medical device of FIG. 1.

FIGS. 1-3 illustrate portions of an exemplary medical device 10. For example, medical device 10 may include biopsy forceps, graspers, baskets, snares, probes, scissors, retrieval devices, lasers, illumination systems and/or other tools. By way of example only, medical device 10 will be described in reference to a basket hereafter. Medical device 10 may include a sheath 12 including a distal end and a proximal end. Medical device 10 may also include an end effector 14 at the distal end of sheath 12. In examples in which medical device 10 comprises a basket, end effector 14 may comprise a cage or basket configured to capture and/or retrieve material. The cage or basket may be laser cut from a tube and/or chemically etched, and be comprised of any appropriate material, such as, for example, shape memory materials including synthetic plastics, stainless steel, and superelastic metallic alloys of nickel/titanium (e.g., Nitinol), copper, cobalt, vanadium, chromium, iron, or the like; or alternative materials including, for example, other metal alloys, powdered metals, ceramics, thermal plastic composites, ceramic composites, and polymers. Also, combinations of these and other materials can be used.

At least a portion of end effector 14 may be movable relative to sheath 12 between an extended state and a retracted state. Medical device 10 may also include a handle assembly 16 at the proximal end of sheath 12. Handle assembly 16 may include an actuation member 18 for moving end effector 14 between the extended state and the retracted state, as will be described in further detail below. A strain relief member 22 may be coupled to handle assembly 16, and may extend at least partially over a proximal portion of sheath 12. Strain relief member 22 may help prevent sheath 12 from kinking at or near the distal end of handle assembly 16. As shown in FIG. 1, strain relief member 12 may have a varying cross-sectional shape and may comprise a polymer material, metal, or a combination of materials. Alternatively, medical device 10 may not include strain relief 22.

As shown in FIG. 2, sheath 12 may include a longitudinally-extending lumen 20. Sheath 12 may be, for example, a hollow tube. Sheath 12 may be made of a polymer material, metal, or a combination of materials. Medical device 10 may also include a drive member 24. Drive member 24 may extend through lumen 20 of sheath 12. Drive member 24 may be elongated, and may include, for example, a wire, braid, shaft, and/or any other suitable drive member configured to transfer translational and/or rotational forces from its proximal end to its distal end. As shown in FIG. 2, a distal end portion of drive member 24 may be coupled to end effector 14. For example, end effector 14 may comprise a tubular member 26, as will be described in further detail below, which may be configured to receive the distal end portion of drive member 24 therein. Drive member 24 may be secured within tubular member 26 via any appropriate connection mechanism such as, for example, laser welding, adhesives, and/or mechanical fasteners, etc. Alternatively, drive member 24 and end effector 14 may be monolithically formed so as to comprise a continuous one-piece structure. Additionally, in another alternative example, a proximal end of tubular member 26 may extend proximally along sheath 12 and be coupled to actuation member 18 within handle assembly 16. In such an arrangement, drive member 24 may be omitted and tubular member 26 may be used to move end effector 14 between the extended state and the retracted state.

As shown in FIG. 3, handle assembly 16 may include a grip 28 configured to movably receive the actuation member 18 therein. Grip 28 may include one or more baffles 38 (FIG. 1) configured to aid a medical professional with securely grasping grip 28. Any number and arrangement of baffles 38 may be disposed on grip 28. Grip 28 may be hollow and have a semi-circular cross-sectional shape. Actuation member 18 may be configured to be matingly received within grip 28. As shown in FIG. 3, actuation member 18 may include a longitudinally extending member 40 and a distal facing end 42 including a nipple 44. The longitudinally extending member 40 may include a raised surface 46 to ease manipulation of the medical device 10 by the medical professional. For example, the raised surface 46 may comprise a thumb or finger rest.

Nipple 44 may extend distally of distal facing end 42 and be configured to be coupled to a connector 36. For example, nipple 44 and connector 36 may be coupled via any appropriate means such as, for example, a screw fit connection and/or adhesive. Connector 36 may include a male luer fitting. As shown in FIG. 3, drive member 24 may extend proximally through a lumen 50 in connector 36, through a lumen 48 in nipple 44, through a support tube 30 along longitudinally extending member 40, and towards a retention member 32. Retention member 32 may be coupled to grip 28 and may form a vise 52, or any other suitable holding mechanism. When vise 52 closes, holding member drive member 24 may be fixedly coupled relative to grip 28. An end cap 34 may be placed onto proximal ends of retention member 32 and vise 52 to help close vise 52 around drive member 24. Vise 52 and/or retention member 32 may include an externally threaded portion (not shown), and end cap 34 may include complementary internal threading (not shown), such that end cap 34 may be screwed onto retention member 32 and vise 52.

In use, a medical professional may urge raised surface 46 distally relative to grip 28 so as to move end effector 14 between the extended state and the retracted state. For example, a medical professional may hold grip 28 within the palm of their hand with their thumb or finger on raised surface 46. In order to move end effector 14 from the extended state to the retracted state, the medical professional may push, slide, or advance raised surface 46 of actuation member 18 relative to grip 28. Due to the connection of sheath 12 to actuation member 18 via connector 36, moving raised surface 46 distally results in distal movement of sheath 12 over end effector 14. Upon advancement of sheath 12 over end effector 14, end effector 14 transitions (e.g., collapses, compresses, etc.) to its retracted state within lumen 20 of sheath 12.

Figure 4:
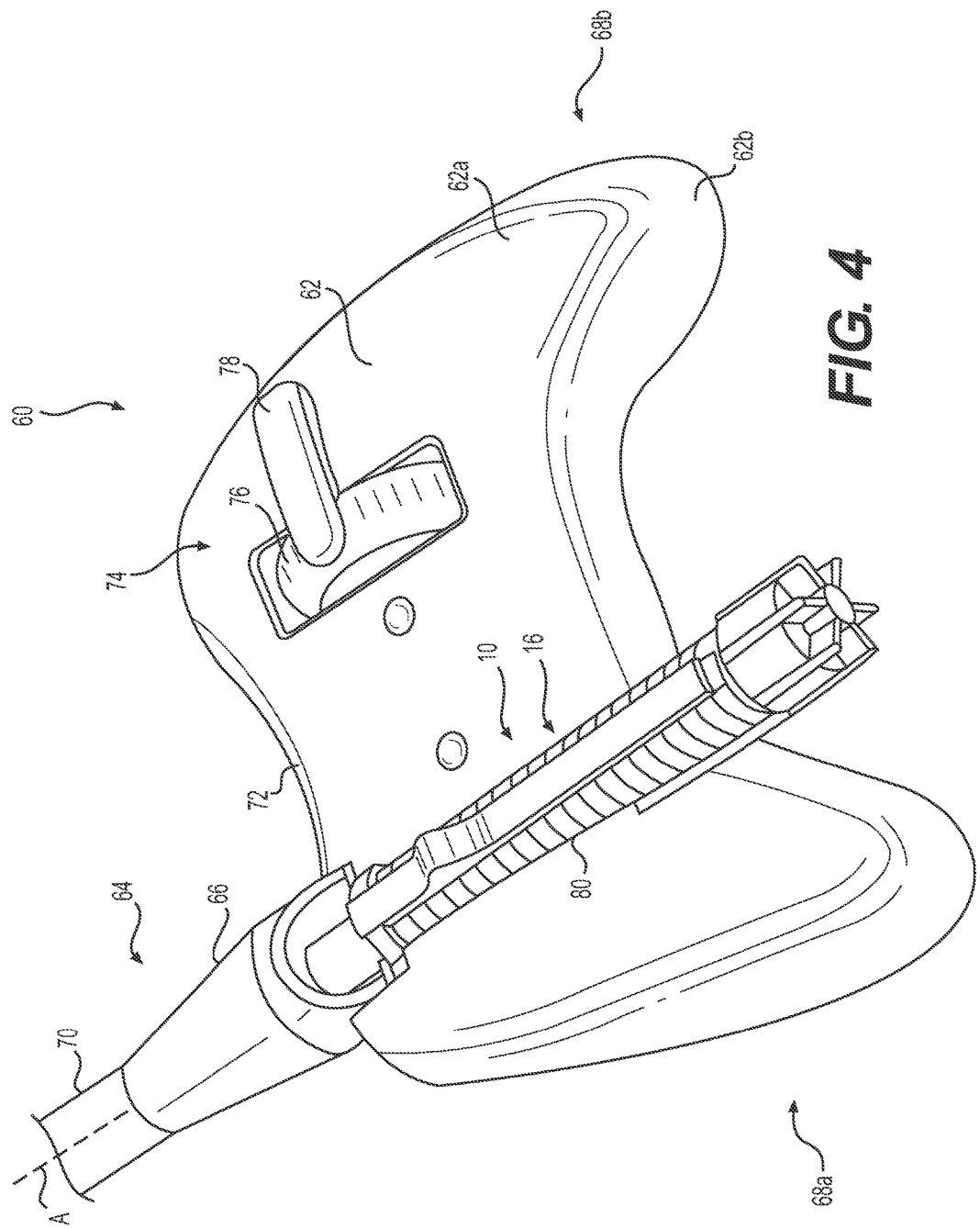
FIG. 4 illustrates an exemplary handle of a scope and/or insertion device for use with the exemplary medical device of FIG. 1.

FIG. 4 shows an exemplary handle 60 of a scope and/or endoscopic insertion device 70. Insertion device 70 may include any device configured to allow a user to perform medical diagnoses and/or treatments on a subject. For example, insertion device 70 may include any device configured to allow a user to access and view internal areas of a subject's body. Additionally or alternatively, insertion device 70 may itself be a medical device and/or include any device configured to deliver medical devices 10, such as, for example, biopsy forceps, graspers, baskets, snares, probes, scissors, retrieval devices, lasers, and/or other tools, into a subject's body. Insertion device 70 may be inserted into one of a variety of body openings, lumens, and/or cavities. For example, the insertion device may be inserted into any portion of a urinary tract, such as a ureter, a gastrointestinal lumen, such as an esophagus, a vascular lumen, and/or an airway.

According to aspects of the present disclosure, insertion device 70 may be a ureteroscope. In some contemplated examples, insertion device 70 may be a sterile, single-use, and disposable ureteroscope. Alternatively, insertion device 70 may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable.

The handle 60 may be formed in any appropriate manner. For example, as shown in FIG. 4, the handle 60 may include a handle housing 62. Handle housing 62 may include a clam shell construction having upper and lower handle housing portions, 62*a* and 62*b*, respectively. At least one of upper and lower handle housing portions 62*a* and 62*b* may be configured to be coupled with the other one of upper and lower handle housing portions 62*a* and 62*b*. For example, upper and lower handle housing portions 62*a* and 62*b* may be joined together by appropriate fasteners, such as, removable fasteners including screws and/or pins, or by non-removable fastening techniques, including heat bonding or adhering with an adhesive. As such, handle 60 may be configured to retain any necessary capital hardware (e.g., push/pull wires and/or linkages for steering, imaging and/or illumination components, one or more printed circuit boards, and/or additional components, etc.).

As shown, handle 60 may be coupled to insertion device 70 via port 64. Port 64 may include any longitudinally-extending member connected to insertion device 70 and handle 60. For example, as shown in FIG. 4, port 64 may define a lumen (not shown) configured to receive at least a portion of medical device 10. In some examples, port 64 may include a tapered side wall 66, while in other examples, the side wall 66 of port 64 may not be tapered. As shown, port 64 may be configured for insertion of medical device 10 into insertion device 70 for delivery therethrough. That is, medical device 10 may be delivered into and through insertion device 70 via port 64 as will be described in further detail below. To facilitate retention of medical device 10 within handle 60, handle 60 may include a groove, slot, channel, and/or passage 80 configured to rotatably receive handle assembly 16 of medical device 10. For example, passage 80 may define an opening within which handle assembly 16 may be retained via any appropriate means such as, for example, via a snap fit connection. Accordingly, passage 80 may securely couple medical device 10 to handle 60 and insertion device 70, while allowing rotation of medical device 10 relative to insertion device 70.

Additionally, handle 60 may include at least one port (not shown) configured to provide access to one or more channels (not shown) extending through insertion device 70. For example, handle 60 may comprise a first port (not shown) configured to communicate a digital camera (not shown) and connecting cord (not shown) therethrough. In some examples, however, the digital camera may be wireless, and accordingly, the first port may not be necessary. Additionally or alternatively, a second port (not shown) may be provided for delivering a suitable fluid, such as a liquid or gas, for irrigation and insufflation purposes, respectively, to and out of a distal portion of insertion device 70. Each of the first and second ports may be positioned along either the 12 o'clock (e.g., top) position or the 6 o'clock (e.g., bottom) position of handle 60 so as not to interfere with handling and/or manipulation of medical device 10 and/or insertion device 70.

As shown in FIG. 4, handle 60 may be configured for ergonomic handling and control by a medical professional. For example, handle 60 may include first and second extensions 68a and 68b extending from base portion 72. Each of first and second extensions 68a and 68b may be configured to be grasped by a respective hand of a medical professional. For example, a medical professional may hold extension 68a in his/her left hand while holding extension 68b in his/her right hand. As such, handle 60, and consequently, insertion device 70, may be securely and comfortably grasped by the medical professional.

As shown in FIG. 4, handle 60 may further include actuator 74 adjacent to one or the other of first and second extensions 68a and 68b, while passage 80 may be positioned adjacent the other of first and second extensions 68a and 68b. Actuator 74 may be mechanically coupled to (e.g., via push/pull wires, linkages, and/or Bowden cables) or otherwise cooperate (e.g., via an electrical servomotor) with the distal portion of insertion member 70 in any conventional manner. Actuator 74 may include a rocking member 76 coupled to a finger and/or thumb rest 78. Manipulation of actuator 74 may deflect, bend, or otherwise adjust the positioning of the distal portion of insertion device 70. For example, distal (e.g., forward) movement of actuator 74 via rest 78 may cause the distal portion of insertion device 70 to move in a first direction (e.g., downward) along a plane. Additionally, proximal (e.g., backward) movement of actuator 74 via rest 78 may cause the distal portion of insertion device 70 to move in a second direction (e.g., upward) along the same plane. It is understood that these directions may be reversed without departing from the scope of this disclosure. For example, distal movement of actuator 74 may result in upward movement of the distal portion of insertion device 70 along the plane, while proximal movement of actuator 74 may result in downward movement of the distal portion of insertion device 70 along the plane. In such a manner, if a medical professional determines a need or desire to alter the positioning of the distal portion of insertion device 70, he/she may do so via actuator 74. While actuator 74 is illustrated as a two-way rocker in FIG. 4, it is understood that actuator 74 may additionally or alternatively comprise a joystick, slider, a push button, and/or other such arrangement. Additionally, while only two-way deflection is described, it is understood that greater of fewer degrees of movement may be achieved. For example, in some arrangements, four-way deflection (e.g., up, down, right, and left) may be achieved via an alternative actuator 74, such as, for example, a joystick.

The ergonomic configuration of the handle 60 provides numerous attributes. For example, since a medical professional is able to hold the handle 60 in line with their forearm and wrist (e.g., hold handle 60 straight out from their forearm and wrist without the need to bend or twist their wrist) in a natural position, the handle assembly 12 decreases carpal tunnel strain. Further, as actuator 74 and medical device 10 may be actuated in line with one another with, for example, a thumb from both hands, medical professional fatigue may be reduced. Additionally, the extensions 68a and 68b of handle 60 enables an ergonomic grasping of insertion device 70 making manipulation of the insertion device 70 increasingly comfortable and user-friendly by keeping the medical professional's wrist in line with a longitudinal axis A of insertion device 70 during rotation and other manipulation of insertion device 70 while being held straight outward. Additionally, the extensions 68a and 68b of handle 60 enable greater rotational freedom along longitudinal axis A as a medical professional can generally rotate his or her arm through a larger range of motion when held straight outward in the natural position with their wrist in line with longitudinal axis A rather than held upright with their wrist sharply bent with respect to longitudinal axis A.

Figure 5:
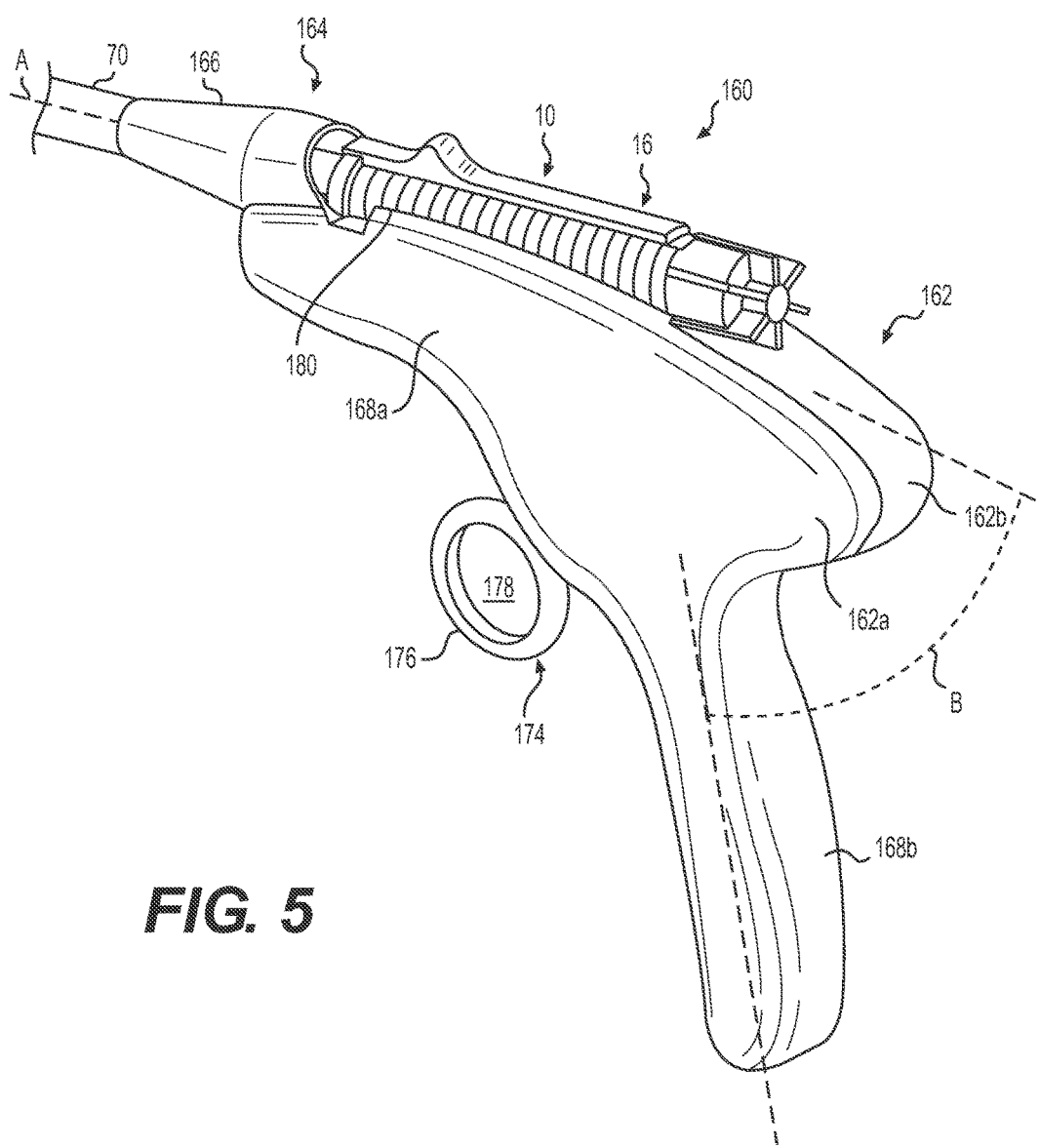
FIG. 5 illustrates another exemplary handle of a scope and/or insertion device for use with the exemplary medical device of FIG. 1.

FIG. 5 illustrates a second exemplary handle 160 of insertion device 70 according to aspects of the disclosure. Handle 160 may be formed in any appropriate manner. For example, handle 160 may include a handle housing 162 comprising a clam shell construction having first and second handle housing portions, 162a and 162b, respectively. At least one of first and second handle housing portions 162a and 162b may be configured to be coupled with the other one of upper and lower handle housing portions 162a and 162b. For example, first and second handle housing portions 162a and 162b may be joined together by appropriate fasteners, such as, removable fasteners including screws and/or pins, or by non-removable fastening techniques, including heat bonding or adhering with an adhesive. As such, handle 160 may be configured to retain any necessary capital hardware (e.g., push/pull wires and/or linkages for steering, imaging and/or illumination components, one or more printed circuit boards, and/or additional components, etc.).

As shown, handle 160 may be coupled to insertion device 70 via port 164. Port 164 may include any longitudinally-extending member connected to insertion device 70 and handle 160. For example, as shown in FIG. 5, port 164 may define a lumen (not shown) configured to receive at least a portion of medical device 10. In some examples, port 164 may include a tapered side wall 166, while in other examples, the side wall 166 of port 164 may not be tapered. As shown, port 164 may be configured for insertion of medical device 10 into insertion device 70 for delivery therethrough. That is, medical device 10 may be delivered into and through insertion device 70 via port 164 as will be described in further detail below. To facilitate retention of medical device 10 within handle 160, handle 160 may include a groove, slot, channel, and/or passage 180 configured to rotatably receive handle assembly 16 of medical device 10. For example, passage 180 may define an opening along an outer surface of handle 160 and within which handle assembly 16 may be retained via any appropriate means such as, for example, via a snap fit connection. Accordingly, passage 180 may securely couple medical device 10 to handle 160 and insertion device 70, while allowing rotation of medical device 10 relative to insertion device 70.

Additionally, handle 160 may include at least one port (not shown) configured to provide access to one or more channels (not shown) extending through insertion device 70. For example, handle 160 may comprise a first port (not shown) configured to communicate with a digital camera (not shown) and connecting cord (not shown) therethrough. The handle 160 also may include fiber optics for illumination to improve visualization. In some examples, however, the digital camera may be wireless, and accordingly, the first port may not be necessary. Additionally or alternatively, a second port (not shown) may be provided for delivering a suitable fluid, such as a liquid or gas, for irrigation and insufflation purposes, respectively, to and out of a distal portion of insertion device 70. Each of the first and second ports may be positioned along either the 12 o'clock (e.g., top) position or the 6 o'clock (e.g., bottom) position of handle 160 so as not to interfere with handling and/or manipulation of medical device 10 and/or insertion device 70.

As shown in FIG. 5, handle 160 may be configured for ergonomic handling and control by a medical professional. For example, handle 160 may include first and second portions 168a and 168b. As shown, the first portion 168a may extend along a longitudinal axis A of insertion device 70, while the second portion 168b may extend at an angle B with respect to longitudinal axis A, thereby forming a pistol-like grip. For example, in some examples, angle B may be about 45°. In other examples, angle B may be between about 0° and about 90°, between about 20° and about 70°, or between about 35° and about 55°. As used herein, the terms "about," "substantially," and "approximately," may indicate a range of values within +/−5% of a stated value.

As shown in FIG. 5, handle 160 may further include actuator 174. Actuator 174 may be mechanically coupled to (e.g., via push/pull wires, linkages, and/or Bowden cables) or otherwise cooperate (e.g., via an electrical servomotor) with the distal portion of insertion member 70 in any conventional manner. Actuator 174 may include a ring, button, and/or trigger 176 configured to be proximally retracted and/or distally advanced by a finger of the medical professional. For example, as shown in FIG. 5, actuator 174 may include a circular hole or opening 178, through which an index or other finger of a medical professional may be inserted. Urging actuator 176 in the distal direction (e.g., forward) may cause the distal portion of insertion device 70 to move in a first direction (e.g., downward) along a plane. Additionally, proximal (e.g., backward) movement of actuator 174 may cause the distal portion of insertion device 70 to move in a second direction (e.g., upward) along the same plane. It is understood that these directions may be reversed without departing from the scope of this disclosure. For example, distal movement of actuator 174 may result in upward movement of the distal portion of insertion device 70 along the plane, while proximal movement of actuator 174 may result in downward movement of the distal portion of insertion device 70 along the plane. In such a manner, if a medical professional determines a need or desire to alter the positioning of the distal portion of insertion device 70, he/she may do so via actuator 174. While actuator 174 is illustrated as a two-way trigger ring in FIG. 5, it is understood that actuator 174 may additionally or alternatively comprise a joystick, slider, a push button, and/or other such arrangement. Additionally, while only two-way deflection is described, it is understood that greater or fewer degrees of movement may be achieved. For example, in some arrangements, four-way deflection (e.g., up, down, right, and left) may be achieved via an alternative actuator 174, such as, for example, a joystick.

Handle 160 provides numerous attributes. For example, since a medical professional is able to hold the handle 160 in line with their forearm in a natural position (e.g., across their waist), the handle 160 decreases carpal tunnel strain. Additionally, the pistol-like grip of handle 160 enables an ergonomic grasping of insertion device 70 making manipulation of the insertion device 70 increasingly comfortable and user-friendly by keeping the medical professional's wrist in line (e.g., parallel) with longitudinal axis A of insertion device 10 during rotation and other manipulation of insertion device 70. The angled or pistol-like grip of handle 160 additionally enables greater rotational freedom along longitudinal axis A as a medical professional can generally rotate his or her arm through a larger range of motion when held in the natural position with their wrist in line (e.g., parallel) with longitudinal axis A rather than held upright with their wrist sharply bent with respect to longitudinal axis A. Finally, the angled or pistol-like grip of the handle 160 may be universally grasped by the medical professional's hand, whether or not they are right-handed or left-handed, thus removing the need for specialized instruments for different medical professionals.

Figure 6:
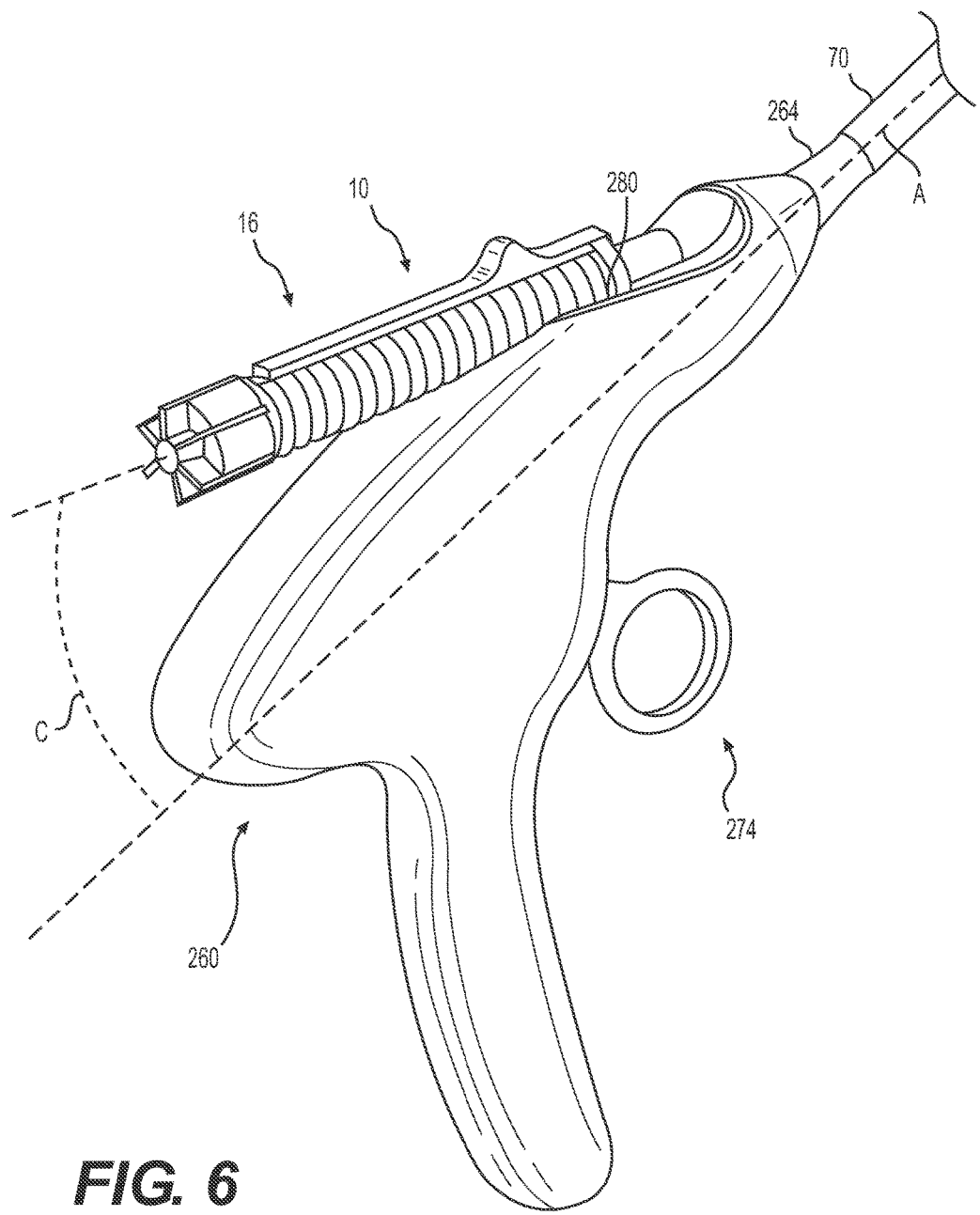
FIG. 6 illustrates still another exemplary handle of a scope and/or insertion device for use with the exemplary medical device of FIG. 1.

FIG. 6 illustrates a third exemplary handle 260 of insertion device 70 according to aspects of the disclosure. Handle 260 is similar in construction and manner of use as handle 160 described in connection with FIG. 5, except that passage 280 is configured to rotationally receive handle assembly 16 of medical device 10 at an angle therein. For example, passage 280 may be configured to support medical device 10 at an angle C relative to longitudinal axis A of insertion device 70. Angle C may be between about 0° and about 45°. By way of example only, angle C may be about 30°. Positioning of medical device 10 at an angle C relative to longitudinal axis A may provide for easier rotation of medical device 10 while coupled to handle 260.

Figure 7:
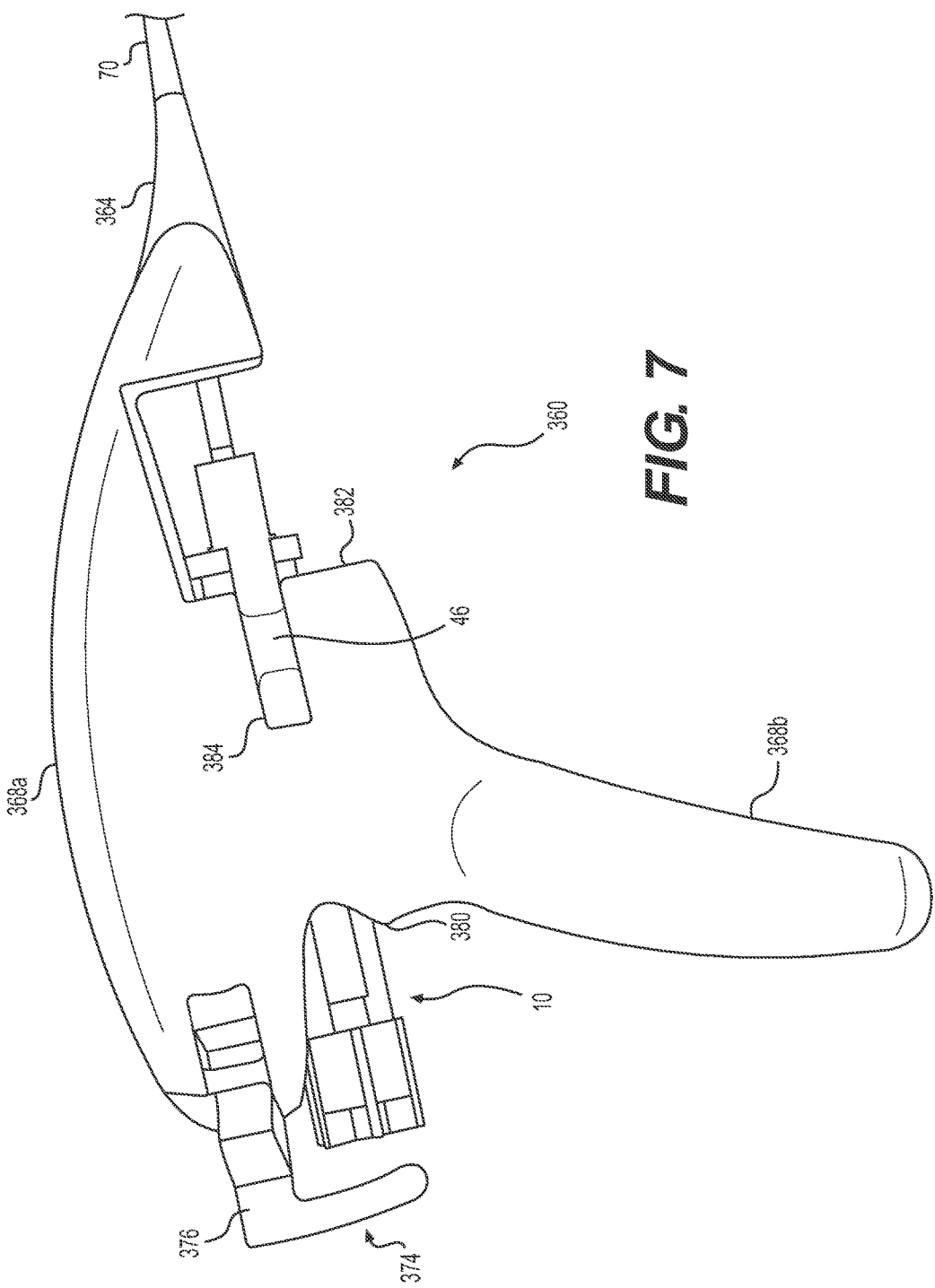
FIG. 7 illustrates still a further exemplary handle of a scope and/or insertion device for use with the exemplary medical device of FIG. 1.

FIG. 7 illustrates a fourth exemplary handle 360 of insertion device 70 according to aspects of the disclosure. Handle 360 is similar in construction and manner of use as handle 160 described in connection with FIG. 5, except that passage 380 is defined through an inner portion of handle 360 and actuator 374 is configured as a side-to-side trigger extending proximally of handle 360.

As shown in FIG. 7, handle 360 may include first and second portions 368a and 368b, respectively. First portion 368a may define passage 380 extending therethrough. Accordingly, passage 380 may comprise a longitudinally-extending internal channel configured to receive medical device 10 therein. In some arrangements, passage 380 may extend through an internal central portion of first portion 368a. Passage 380 may extend between a proximal end of first portion 368a and an opening 382. As shown, opening 382 may define a cut-out through first portion 368a and in communication with passage 380 such that medical device 10 may be back loaded into passage 380 via opening 382. For example, a proximal most end of medical device 10 may be inserted through opening 382 and routed (e.g., advanced, passed, and/or directed) proximally through passage 380. Once positioned within passage 380, medical device 10 may be retained therein via a snap-fit connection. Accordingly, medical device 10 may be prevented from moving distally or proximally once positioned within first portion 368a. Alternatively, medical device 10 may be front loaded into passage 380. That is, a distal most end of medical device 10 may be inserted into a proximal most end of passage 380 and advanced distally therein. In such an arrangement, opening 382 may not be necessary.

As shown in FIG. 7, opening 382 may include a longitudinally extending slot 384 extending proximally from opening 382. Raised surface 46 of medical device 10 may be positioned so as to extend through slot 384. Accordingly, a medical professional may transition the medical device 10 between the extended state and a retracted state via actuation of the raised surface 46 within slot 384.

As shown in FIG. 7, handle 360 may further include actuator 374. Actuator 374 may be mechanically coupled to (e.g., via push/pull wires, linkages, and/or Bowden cables) or otherwise cooperate (e.g., via an electrical servomotor) with the distal portion of insertion member 70 in any conventional manner. Actuator 374 may include a trigger 376 configured to be actuated back and forth by a finger of the medical professional. For example, urging actuator 374 towards the right (e.g., out of the page of FIG. 7) may cause the distal portion of insertion device 70 to move in a first direction (e.g., rightward) along a plane. Additionally, urging actuator 374 towards the left (e.g., into the page of FIG. 7) may cause the distal portion of insertion device 70 to move in a second direction (e.g., leftward) along the same plane. It is understood that these directions may be reversed without departing from the scope of this disclosure. For example, rightward movement of actuator 374 may result in leftward movement of the distal portion of insertion device 70 along the plane, while leftward movement of actuator 374 may result in rightward movement of the distal portion of insertion device 70 along the plane. In such a manner, if a medical professional determines a need or desire to alter the positioning of the distal portion of insertion device 70, he/she may do so via actuator 374. While actuator 374 is illustrated as a two-way trigger button in FIG. 7, it is understood that actuator 374 may additionally or alternatively comprise a joystick, slider, a push button, and/or other such arrangement. Additionally, while only two-way deflection is described, it is understood that greater of fewer degrees of movement may be achieved. For example, in some arrangements, four-way deflection (e.g., up, down, right, and left) may be achieved via an alternative actuator 374, such as, for example, a joystick.

Figure 8:
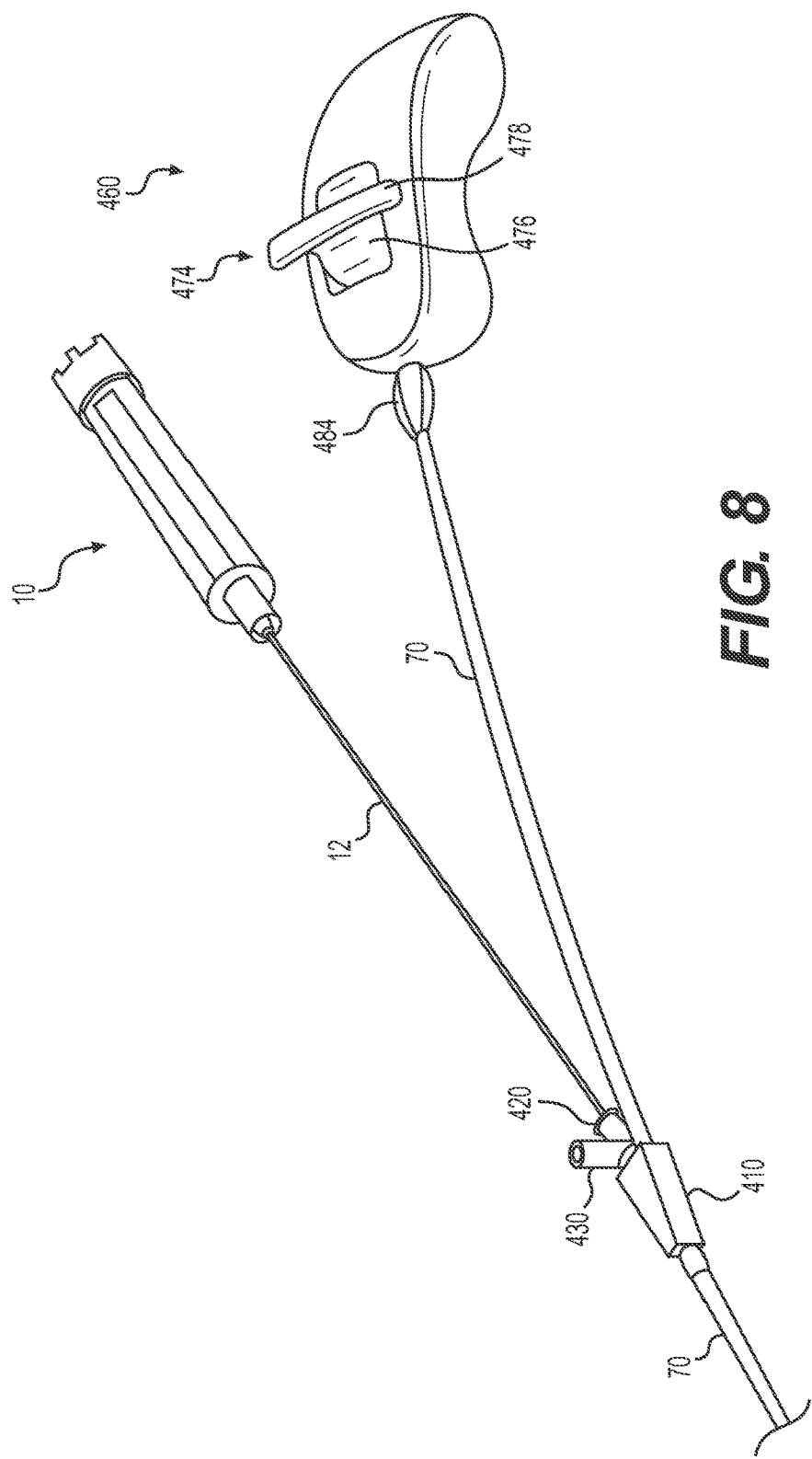
FIG. 8 illustrates another exemplary handle of a scope and/or insertion device for use with the exemplary medical device of FIG. 1.

FIG. 8 illustrates a fifth exemplary handle 460 of insertion device 70 according to aspects of the disclosure. As shown, handle 460 may be coupled to insertion device 70 via a coupler 484 while medical device 10 may be coupled to insertion device via connection 410. Connection 410 may comprise a luer or any other fluid coupling positioned along insertion device 70. Connection 410 may include a first port 420 and a second port 430. Ports 420 and 430 may provide access to one or more channels (not shown) extending through insertion device 70. As shown, first port 420 may be configured to receive at least a portion of medical device 10 therethrough. For example, first port 420 may be configured to receive the sheath 12 of medical device 10 therethrough. Second port 430 may provide access into one or more working channels of insertion device 70 for delivering a suitable fluid, such as a liquid or gas, for irrigation and insufflation purposes, respectively, to and out of the distal portion of insertion device 70. It is also contemplated that second port 430 may be in fluid communication with one or more working channels for withdrawing material from insertion device 70 and/or an area near the distal portion of insertion device 70, using suction.

As shown in FIG. 8, handle 460 may further include actuator 474. Actuator 474 may be mechanically coupled to (e.g., via push/pull wires, linkages, and/or Bowden cables) or otherwise cooperate (e.g., via an electrical servomotor) with the distal portion of insertion member 70 in any conventional manner. Actuator 474 may include a rocking member 476 coupled to a finger and/or thumb rest 478. Manipulation of actuator 474 may deflect, bend, or otherwise adjust the positioning of a distal portion of insertion device 70. For example, distal (e.g., forward) movement of actuator 474 via rest 478 may cause the distal portion of insertion device 70 to move in a first direction (e.g., downward) along a plane. Additionally, proximal (e.g., backward) movement of actuator 474 via rest 478 may cause the distal portion of insertion device 70 to move in a second direction (e.g., upward) along the same plane. It is understood that these directions may be reversed without departing from the scope of this disclosure. For example, distal movement of actuator 474 may result in upward movement of the distal portion of insertion device 70 along the plane, while proximal movement of actuator 474 may result in downward movement of the distal portion of insertion device 70 along the plane. In such a manner, if a medical professional determines a need or desire to alter the positioning of the distal portion of insertion device 70, he/she may do so via actuator 474. While actuator 474 is illustrated as a two-way rocker in FIG. 8, it is understood that actuator 474 may additionally or alternatively comprise a joystick, slider, a push button, and/or other such arrangement. Additionally, while only two-way deflection is described, it is understood that greater of fewer degrees of movement may be achieved. For example, in some arrangements, four-way deflection (e.g., up, down, right, and left) may be achieved via an alternative actuator 474, such as, for example, a joystick.

In use, a medical professional may insert insertion device 70 into the body of a patient. For example, the distal portion of insertion device 70 may be inserted through the urethral meatus of the ureter and may be used to hold urethral meatus. Once inserted, the medical professional may optionally deflect the distal portion of insertion device 70 as necessary to direct the distal portion of insertion device 70 towards an area or object of interest within the body of the patient. As such, the medical professional may rotate insertion device 70 through a desired angular range of motion and/or manipulate actuator 74, 174, 274, 374, or 474 to bend, deflect, or otherwise move the distal portion of insertion device 70 as desired.

If the medical professional determines there is a need for the insertion of medical device 10, he or she may insert said device through insertion device 70 as described above. For example, the medical professional may use one hand, for example, the dominant hand, to maintain a grasp on insertion device 70 while using his or her second hand, for example, the non-dominant hand, to position medical device 10 through port 64, 164, 264, 364, or 420.

Once a distal end of medical device 10, e.g., a basket, is extended distally of the distal portion of insertion device 70, a medical professional may actuate the basket to open so as to be configured to receive an object therein. To do so, the medical professional may urge actuation member 18 to cause end-effector 14 to radially expand to open and receive a stone or other material therein. If the medical professional needs to redirect or aim the basket to a different orientation, he or she may rotate the handle assembly 16 of medical device 10, and thereby end-effector 14 so as to re-orient end-effector 14 as needed. Once at the desired position, the medical professional may treat the patient with medical device 10 by, for example, capturing a stone or other material within the end effector 14. Once a desired treatment is completed, a medical professional may withdraw or remove medical device 10 and/or insertion device 70.

Insertion device 70 and medical device 10 provide numerous attributes. For example, insertion device 70 and medical device 10 may be operated by the dominant and non-dominant hand, or vice versa, respectively, of a single medical professional. Accordingly, the need for precise communication between the medical professional and any assistants is reduced as the entire procedure may be performed by a single operator. Indeed, as the dominant hand, for example, may remain on insertion device 70 throughout operation, the medical professional may maintain numerous degrees of freedom of insertion device 70. Additionally, the time necessitated by a medical procedure may be reduced since time spent advising and/or instructing an assistant may be reduced.

Further, since a medical professional is able to hold handles 60, 160, 260, 360, and 460 in line (e.g., straight out from their forearm and wrist without the need to bend or twist their wrist; and/or parallel) with their forearm in a natural position, handles 60, 160, 260, 360, and 460 may decrease carpal tunnel strain. Additionally, handles 60, 160, 260, 360, and 460 enable an ergonomic grasping of insertion device 70 making manipulation of insertion device 70 increasingly comfortable and user-friendly by keeping the medical professional's wrist in line with longitudinal axis A of insertion device 70 during rotation and other manipulation of insertion device 70. Handles 60, 160, 260, 360, and 460 additionally enable greater rotational freedom along longitudinal axis A as a medical professional can generally rotate his or her arm through a larger range of motion when held in the natural position with their wrist in line with longitudinal axis A rather than held upright with their wrist sharply bent with respect to longitudinal axis A. Further, handles 60, 160, 260, 360, and 460 may be universally grasped by the medical professional's hand, whether or not they are right-handed or left-handed, thus removing the need for specialized instruments for different medical professionals. Finally, since insertion device 70 is configured to be held in the natural position with their wrist in line (e.g. parallel) with longitudinal axis A, the movement of the distal portion of insertion device 70 may be made more intuitive than conventional insertion devices by mimicking the pointing and flexing of the medical professional's index finger.

Accordingly, the described insertion device 70 and medical device 10 provide a medical professional command and control of numerous aspects of the medical system throughout a procedure thus enhancing procedure efficiency and reducing the number of hands/people required for completion of the procedure. Additionally, it is understood that the disclosed medical device 10 and handles 60, 160, 260, 360, and 460 may be used in conjunction with any scope and/or insertion device readily available. For example, medical device 10 and handles 60, 160, 260, 360, and 460 may be used with a conventional scope and/or insertion device 70, such as any flexible, semi-rigid, and/or rigid insertion device.

While principles of the present disclosure are described herein with reference to illustrative examples for particular applications, it should be understood that the disclosure is not limited thereto. Those having ordinary skill in the art and access to the teachings provided herein will recognize additional modifications, applications, examples, and substitution of equivalents all fall within the scope of the examples described herein. Accordingly, the invention is not to be considered as limited by the foregoing description.

We claim:

1. An endoscopic apparatus, comprising:
    a handle comprising a first portion and a second portion, wherein the second portion extends at an angle from the first portion, wherein the handle comprises:
        a passage defined by the first portion; and
        an actuator operably coupled to the first portion;
    an insertion device coupled to and extending distally of the first portion of the handle, wherein the insertion device includes a central longitudinal axis collinear with a central longitudinal axis of the first portion; and
    a medical device extending through the passage and at least partially received within a lumen of the insertion device;
    wherein the manipulation of the actuator is configured to deflect a distal portion of the insertion device.

2. The endoscopic apparatus of claim 1, wherein the angle is between about 35° and about 55°.

3. The endoscopic apparatus of claim 1, wherein the passage is defined along an outer surface of the first portion.

4. The endoscopic apparatus of claim 1, wherein the passage is configured to receive the medical device therein along an angle relative to a longitudinal axis of the insertion device.

5. The endoscopic apparatus of claim 4, wherein the angle relative to the longitudinal axis of the insertion device is between about 0° and about 45°.

6. The endoscopic apparatus of claim 1, wherein the passage is configured to rotatably receive the medical device therein.

7. The endoscopic apparatus of claim 1, wherein the actuator is configured for at least two-way deflection of the distal portion of the insertion device.

8. The endoscopic apparatus of claim 1, wherein the passage is configured to receive the medical device therein via a snap-fit connection.

9. The endoscopic apparatus of claim 1, wherein the passage extends through an inner central portion of the first portion of the handle.

10. The endoscopic apparatus of claim 9, further comprising:
    an opening extending through the first portion of the handle, the opening being in communication with the passage.

11. The endoscopic apparatus of claim 10, further comprising:
    a slot extending proximally from a proximal end of the opening and configured to receive an actuation mechanism of the medical device therein.

12. An endoscopic apparatus, comprising:
    a handle comprising a handle housing, the handle housing defining a central base portion, a first extension, and a second extension, the first extension and the second extension extending from opposite sides of the base portion and configured to be grasped by opposite hands of a user, wherein the handle comprises:
        a passage positioned adjacent to one of the first extension or the second extension; and an actuator positioned adjacent to another of the first extension or the second extension;

an insertion device coupled to and extending distally of the one of the first extension or the second extension of the handle; and a medical device rotatably received within the passage and a lumen of the insertion device;

wherein manipulation of the actuator is configured to deflect a distal portion of the insertion device.

13. The endoscopic apparatus of claim 12, wherein the actuator is configured for at least two-way deflection of the distal portion of the insertion device.

14. The endoscopic apparatus of claim 12, wherein the passage is configured to receive the medical device therein via a snap-fit connection.

15. The endoscopic apparatus of claim 12, wherein the handle comprises a two-part construction in which a first part and a second part are coupled via at least one fastener.

16. The endoscopic apparatus of claim 12, wherein the medical device comprises a retrieval basket or a laser fiber.

17. The endoscopic device of claim 12, wherein a longitudinal axis of the actuator is parallel with a longitudinal axis of the insertion device.

18. A method, comprising:
delivering an endoscopic insertion device into an anatomical opening, the insertion device having a deflectable distal portion and a proximal handle, the proximal handle including;
a first portion and a second portion, wherein the second portion extends at an angle from the first portion,
a passage configured to receive a medical device therethrough defined by the first portion, and
an actuator operably coupled to the first portion;
manipulating the deflectable distal portion via the actuator;
advancing a medical device through a lumen of the insertion device to a location distal of the distal portion of the insertion device; and
transitioning the medical device between a radially retracted state and a radially expanded state relative to a longitudinal axis of the medical device.

19. The method of claim 18, wherein the medical device comprises a basket including a plurality of legs, and the method further includes:
capturing an object within the plurality of legs of the basket.

20. The method of claim 18, wherein the passage is configured to rotatably receive the medical device therein.

* * * * *